(12) United States Patent 
Inoue et al.

(10) Patent No.: US 8,413,650 B2
(45) Date of Patent: Apr. 9, 2013

(54) INHALER

(75) Inventors: Sachiko Inoue, Kawasaki (JP); Hideki Kaneko, Yokohama (JP); Masaru Sugita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 950 days.

(21) Appl. No.: 12/497,253

(22) Filed: Jul. 2, 2009

(65) Prior Publication Data

US 2010/0000527 A1 Jan. 7, 2010

(30) Foreign Application Priority Data

Jul. 4, 2008 (JP) ................................ 2008-175333

(51) Int. Cl.
*A61M 11/00* (2006.01)
(52) U.S. Cl. ....... 128/200.23; 128/203.151; 128/203.21; 128/203.23; 128/203.24; 128/203.14
(58) Field of Classification Search ............ 128/200.23, 128/203.14, 203.15, 203.21, 203.23, 203.24
See application file for complete search history.

(56) References Cited

U.S. PATENT DOCUMENTS

| | | | | |
|---|---|---|---|---|
| 5,035,237 A | * | 7/1991 | Newell et al. ............ | 128/203.15 |
| 5,337,740 A | * | 8/1994 | Armstrong et al. ...... | 128/203.12 |
| 2002/0000225 A1 | * | 1/2002 | Schuler et al. ........... | 128/200.14 |
| 2007/0163576 A1 | * | 7/2007 | Bacon ...................... | 128/200.23 |
| 2009/0283094 A1 | | 11/2009 | Hamano et al. .......... | 128/203.15 |

FOREIGN PATENT DOCUMENTS

| | | |
|---|---|---|
| JP | 2004-283244 | 10/2004 |
| JP | 2004-350976 | 12/2004 |
| WO | WO 95/01137 | 1/1995 |
| WO | WO 02/04043 | 1/2002 |

\* cited by examiner

*Primary Examiner* — Lynne Anderson
*Assistant Examiner* — Bradley Philips
(74) *Attorney, Agent, or Firm* — Fitzpatrick, Cella, Harper & Scinto

(57) ABSTRACT

A user inhales medicine ejected from the medicine ejecting section of an inhaler into the air flow duct of an air flow duct forming member through a hole. As the air flow duct forming member is taken off from the inhaler body, the medicine ejecting section is covered by a cap for protection. As the air flow duct forming member is fitted to the inhaler body, the cap is opened and a sensor recognizes the open state of the cap so that the air flow duct forming member is prohibited from being fitted to and taken off from the inhaler body by a claw that is secured to the air flow duct forming member. In this way, the medicine ejecting section is prevented from being damaged when the air flow duct is fitted to and taken away from the inhaler.

3 Claims, 6 Drawing Sheets

INHALER

BACKGROUND OF THE INVENTION

1. Field of the Invention

The present invention relates to an inhaler for ejecting medicine as micro-droplets and causing a user to inhale the medicine.

2. Description of the Related Art

There has been and still is a longstanding unmet demand for means for ejecting medicine as micro-droplets and administering the medicine to a user at his or her windpipe and lungs and a convenient method of causing medicine to be absorbed from lungs instead of subcutaneously injecting the medicine in order to make it easy for a user or a patient to administer medicine by him or herself. To meet the demand, inhalers designed to generate bubbles in medicine by means of a heater element arranged in an ejection head and eject medicine-containing-liquid under the pressure of the generated bubbles so as to eject the medicine as micro-droplets into the air flow to be inhaled by the patient via the patient's mouth have been developed (see International Publication Nos. WO95/01137 and WO02/04043).

If an ejection head for ejecting medicine is to be operated for a number of times and such an ejection head is exposed to air when it is not in use, dust can adhere to the ejection port(s) and the medicine disposed at and near the ejection port(s) contacts air and may coagulate to give rise to an undesirable situation.

Japanese Patent Application Laid-Open No. 2004-283244 discloses a cap that operates as a unit for protecting the medicine ejecting section of such an ejection head when the head is not in use.

An arrangement of providing a cap that can automatically be opened and closed as a unit for protecting the medicine ejecting section of an ejection head is also known (see Japanese Patent Application Laid-Open No. 2004-350976).

In such inhalers, an inhalation port by way of which a user inhales medicine is arranged at an end of the inhaler and connected to an air flow duct that leads medicine to the inhalation port by means of the air flow produced by the user trying to inhale medicine. The part of the inhaler where the ejected medicine passes can be cleaned if the inhalation port that is held in the user's mouth and the air flow duct for leading the ejected medicine to the inhalation port are removable. However, if the air flow duct is removable, the medicine ejecting section of the inhaler that is structurally located near the air flow duct can be damaged when removing the air flow duct and also when putting it back.

The cap for protecting the ejecting section as described above is designed to be opened and closed by a user. However, an operation of opening and closing such a cap is cumbersome to the user and the user can damage the ejecting section when he or she is opening or closing the cap. While such a cap can be realized as an automatic cap that is opened and closed automatically as described above, the ejecting section can be damaged if the air flow duct is removed by error when the cap is open. Thus, while Japanese Patent Applications Laid-Open Nos. 2004-283244 and 2004-350976 disclose protection caps as a unit for protecting the medicine ejecting section of an inhaler, they do not take the risk of damaging the medicine ejecting section in an operation of putting the removable air flow duct in position or taking the air flow duct out into consideration.

SUMMARY OF THE INVENTION

In view of the above-identified circumstances, it is therefore the object of the present invention to provide an inhaler that can prevent the medicine ejecting section thereof from being damaged when an air flow duct forming member is fitted to and removed from the inhaler body.

In the first aspect of the present invention, the above object is achieved by providing an inhaler to be used by a user to inhale medicine, the inhaler including: an inhaler body having a medicine ejecting section for ejecting medicine; an air flow duct forming member having an inhalation port and adapted to be removably fitted to the inhaler body so as to form an air flow duct on the inhaler body in order to lead the medicine ejected from the medicine ejecting section to the inhalation port; a cap adapted to be freely opened and closed so as to protect the medicine ejecting section at rest; an opening/closing mechanism for opening and closing the cap; and a locking mechanism for prohibiting the air flow duct forming member from being fitted to and removed from the inhaler body when the cap is open and not protecting the medicine ejecting section.

In the second aspect of the present invention, there is provided an inhaler to be used by a user to inhale medicine, the inhaler including: an inhaler body having a medicine ejecting section for ejecting medicine; an air flow duct forming member having an inhalation port and adapted to be removably fitted to the inhaler body so as to form an air flow duct on the inhaler body in order to lead the medicine ejected from the medicine ejecting section to the inhalation port; a cap adapted to be freely opened and closed so as to protect the medicine ejecting section at rest; and an opening/closing mechanism adapted to recognize the air flow duct forming member fitted to or removed from the inhaler body and open or close, whichever appropriate, the cap accordingly.

In the third aspect of the present invention, there is provided an inhaler to be used by a user to inhale medicine, the inhaler including: an inhaler body having a medicine ejecting section for ejecting medicine; an air flow duct forming member having an inhalation port and adapted to be removably fitted to the inhaler body so as to form an air flow duct on the inhaler body in order to lead the medicine ejected from the medicine ejecting section to the inhalation port; a cap adapted to be freely opened and closed so as to protect the medicine ejecting section at rest; and an interlocking mechanism for opening or closing the cap in response to an operation of fitting the air flow duct forming member to or removing the air flow duct forming member from, whichever appropriate, the inhaler body.

With any of the above-described arrangements according to the present invention, the air flow duct forming member is locked relative to the inhaler body and prohibited from being fitted to or removed from the latter when the cap is not protecting the medicine ejecting section. Thus, the medicine ejecting section is not damaged when the air flow duct forming member is fitted to and removed from the inhaler body.

A warning mechanism may be provided to notify the user that the air flow duct forming member is locked relative to the inhaler body and the user is prohibited from fitting the air flow duct forming member to and removing the air flow duct forming member from the inhaler body when the cap is not protecting the medicine ejecting section.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 1A and 1B schematically illustrate the inhaler of Example 1, FIG. 1A is a schematic cross-sectional view of the inhaler and FIG. 1B is a flowchart illustrating the operation of the locking mechanism for prohibiting the air flow duct forming member from being fitted to and taken off from the inhaler body.

FIGS. 2A and 2B schematically illustrate the inhaler of Example 2, FIG. 2A is a schematic cross-sectional view of the inhaler and FIG. 2B is a flowchart illustrating the operation of the locking mechanism for prohibiting the air flow duct forming member from being fitted to and taken off from the inhaler body.

Figure 3:
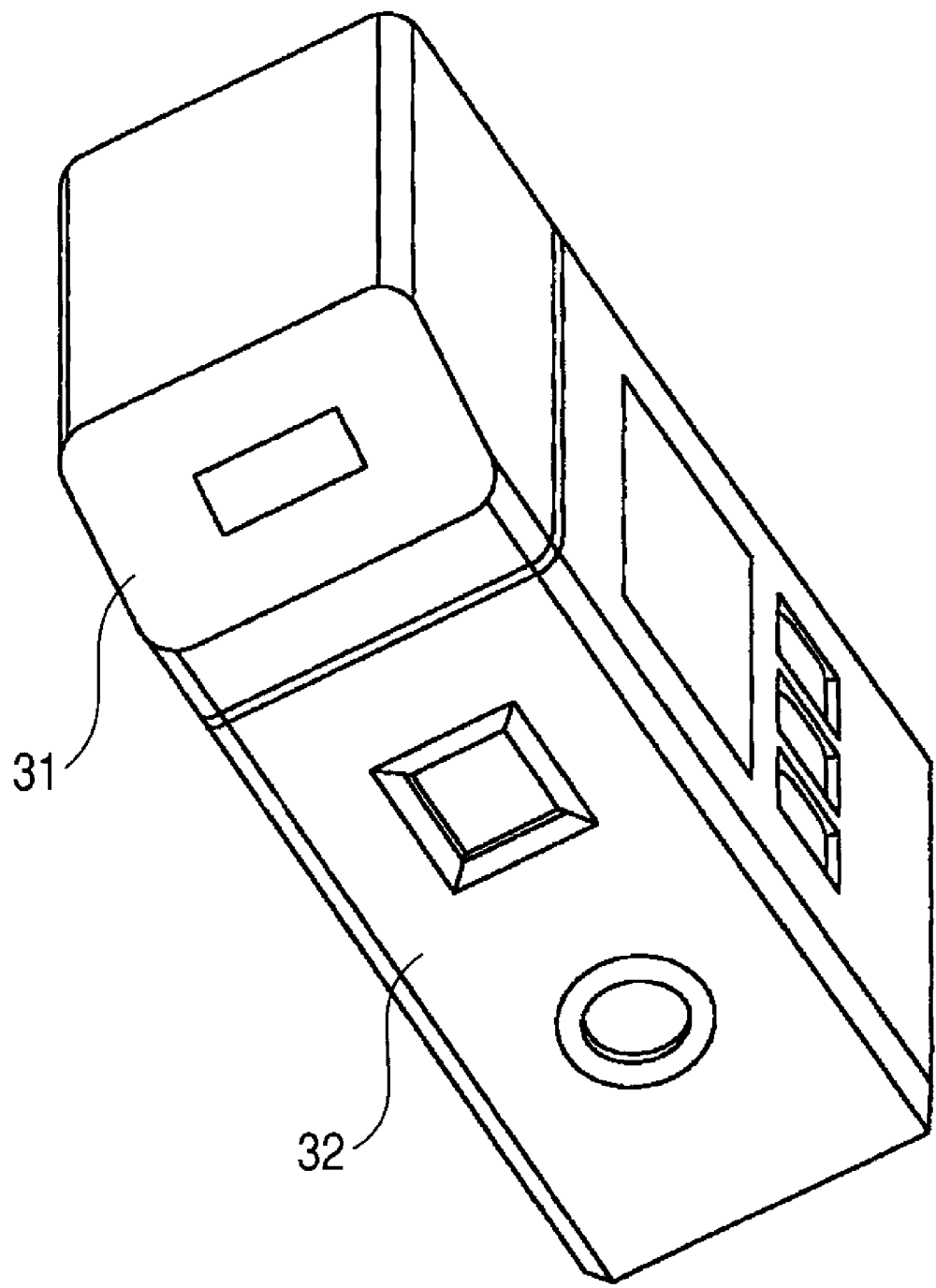
FIG. 3 is a schematic perspective view of the inhaler of Example 3.
Figure 5A:
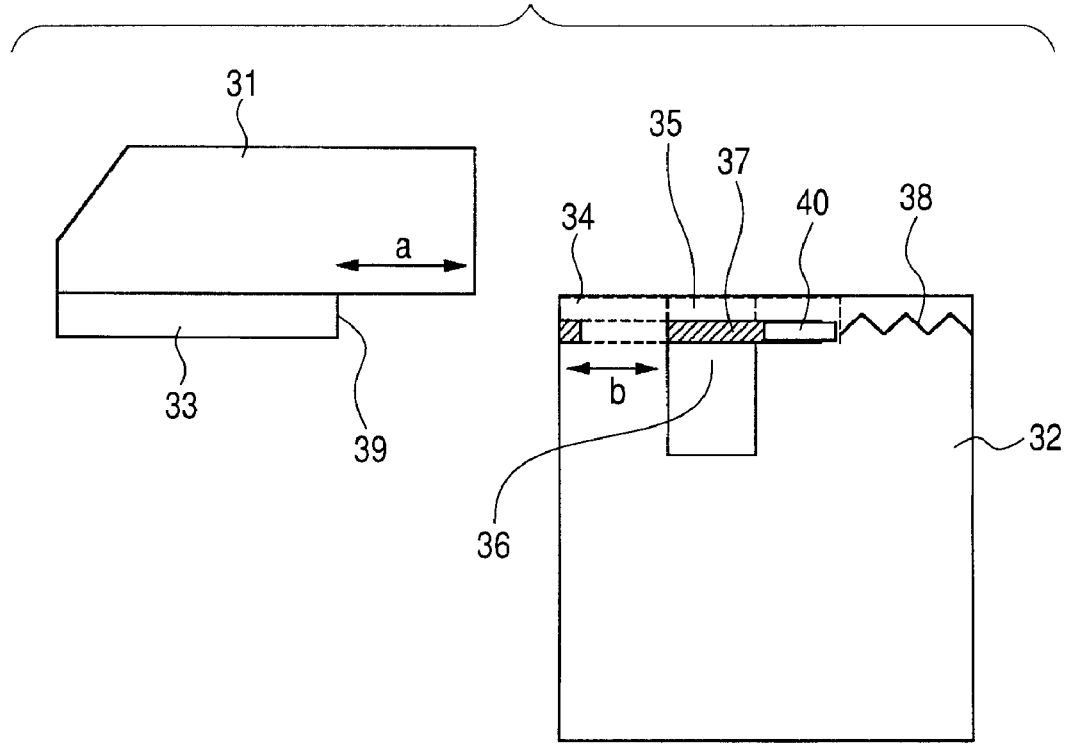
Figure 5B:
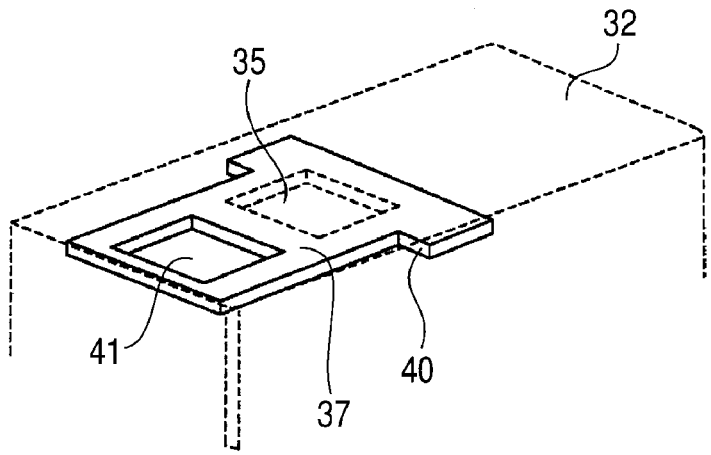

FIGS. 5A and 5B schematically illustrate the inhaler of FIG. 3 from which the air flow duct forming member is taken off, FIG. 5A is a schematic cross-sectional view thereof and FIG. 5B is a partial perspective view illustrating only an upper part of the inhaler body.

Figure 6A:
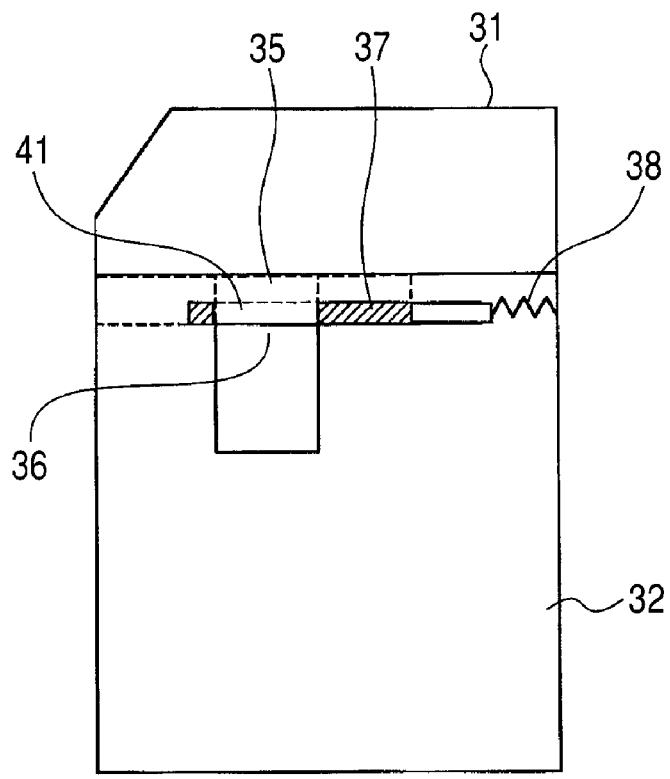
Figure 6B:
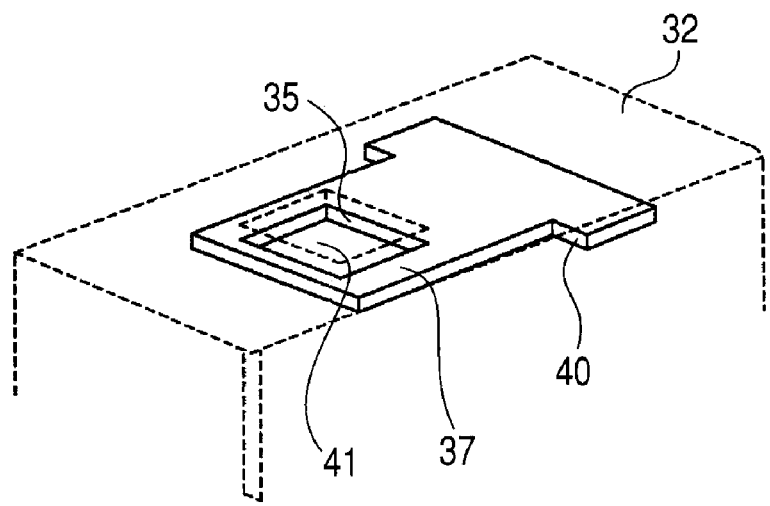

FIGS. 6A and 6B schematically illustrate the inhaler of FIG. 3 with the air flow duct forming member fitted thereto, FIG. 6A is a schematic cross-sectional view thereof and FIG. 6B is a schematic perspective view of only an upper part of the inhaler body.

DESCRIPTION OF THE EMBODIMENTS

Exemplary embodiments of the present invention will now be described in detail in accordance with the accompanying drawings.

EXAMPLE 1

Figure 1A:
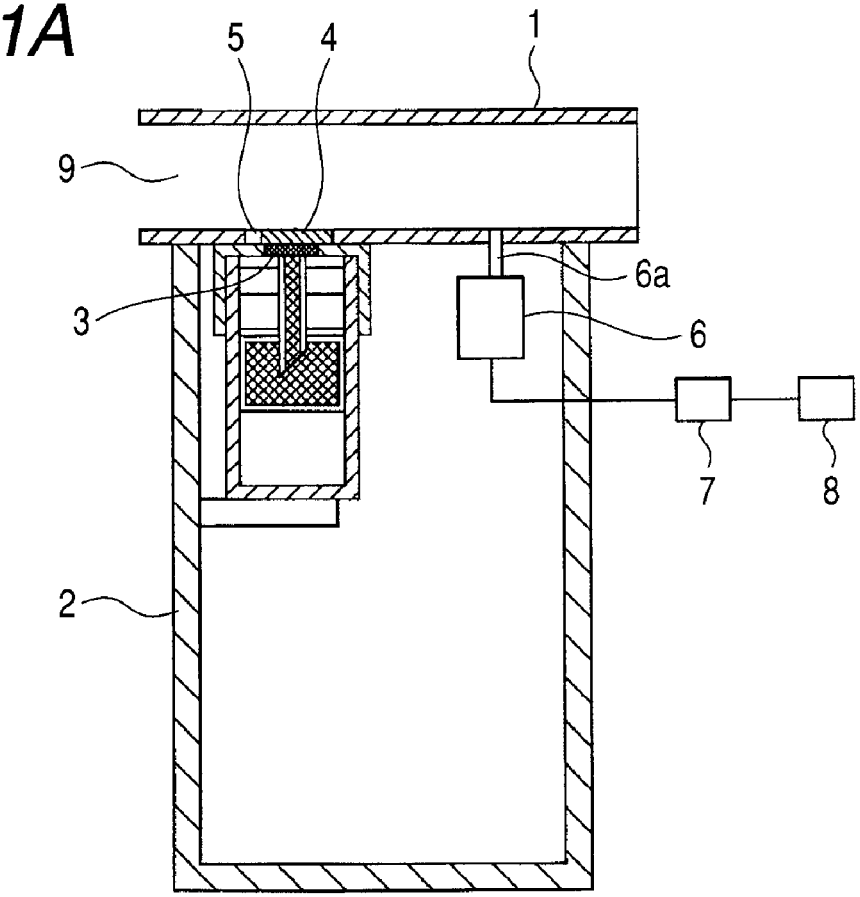

FIG. 1A is a schematic cross-sectional view of the inhaler of Example 1. The inhaler includes an air flow duct forming member 1 that forms an air flow duct for leading the ejected medicine to the inhalation port thereof and an inhaler body 2 that removably holds the air flow duct forming member 1. The inhaler body 2 by turn includes a medicine ejecting section 3 that ejects medicine. The inhaler body 2 further includes a cap 4 that protects the medicine ejecting section 3 and that can be freely opened and closed, an opening/closing mechanism (not shown) for opening and closing the cap, a sensor 5 for recognizing if the cap is protecting the medicine ejecting section 3 or not and a locking mechanism 6 for prohibiting the air flow duct forming member 1 from being fitted to or removed from the inhaler body 2 as well as a warning mechanism 7 for notifying the user that the air flow duct forming member 1 that forms an air flow duct on the inhaler body is prohibited from being fitted to and removed from the inhaler body 2, and a CPU 8. The medicine ejecting section 3 is arranged so as to face the inner wall of the air flow duct forming member 1 in order to lead the medicine ejected from the medicine ejecting section 3 by means of an inhalation air flow to the user in the air flow duct formed by the air flow duct forming member 1.

The user puts the air flow duct forming member 1 into his or her mouth or nose to inhale medicine. The air flow duct forming member 1 can be removed from the inhaler body 2 in order to clean the part thereof through which the ejected liquid passes.

When the air flow duct forming member becomes worn or damaged, the air flow duct forming member can be replaced by a new air flow duct forming member. Furthermore, the air flow duct forming member can be customized so as to show an optimal profile that meets the user's taste and/or is convenient to the user.

When the inhaler is at rest and hence not operated for inhaling medicine, the air flow duct forming member 1 may be taken off from the inhaler body 2 or held to the inhaler body 2. Preferably, the air flow duct forming member 1 has a structure where the hole 9 that operates as inhalation port through which liquid medicine that is put into the user's mouth or nose comes out is sufficiently small so that the user may not be able to put any of his or her fingers or something that can damage the medicine ejecting section 3 into the air flow duct through the hole 9.

The air flow duct forming member 1 is so arranged that the user can put it to and remove it from the inhaler body 2 by moving it horizontally or vertically or rotating it.

The locking mechanism 6 that locks the air flow duct forming member 1 relative to the inhaler body 2 and prohibits the air flow duct forming member 1 from being fitted to or removed from the inhaler body 2 is so structured as to prevent the air flow duct forming member 1 from moving in horizontal directions and vertical directions and rotating in any direction. For instance, the user can remove the air flow duct forming member 1 from the inhaler body 2 by moving the air flow duct forming member 1 horizontally toward the right side in FIG. 1A. Likewise, the user can fit the air flow duct forming member 1 removed from the inhaler body 2 to the latter once again by moving the air flow duct forming member 1 horizontally toward the left side in FIG. 1A. The locking mechanism 6 for prohibiting the air flow duct forming member 1 from being fitted to and removed from the inhaler body 2 is so designed as to move a claw 6a vertically by means of a motor or a solenoid valve and lock the air flow duct forming member 1 to the inhaler body so as to prevent the air flow duct forming member 1 from being translated.

The medicine ejecting section 3 includes an ejection head having a plurality of ejection ports. One or more than one element for generating energy necessary for ejecting medicine are arranged corresponding to the plurality of ejection ports on a one to one basis, on a one to many basis or on a many to one basis. For instance, one or more than one electrothermal transducers such as micro-heaters are arranged in the case of ejecting medicine by applying heat to the medicine, using the principle of thermal ink-jet ejection. The ejection head may alternatively be a piezoelectric ink-jet type ejection head that employs one or more than one piezoelectric elements as so many electromechanical transducers. A cap is highly preferably provided to hermetically seal and protect the ejection ports at rest for an arrangement having a multiple of micro ejection ports. The cap 4 for protecting the medicine ejecting section 3 covers the plane of the ejection ports for the purpose of protecting the medicine ejecting section 3.

When the cap 4 is closed to cover the medicine ejecting section 3, the sensor 5 recognizes that the cap 4 is protecting the medicine ejecting section 3.

The sensor 5 is typically a touch sensor or a photo-sensor that is adapted to transmit an electric signal that represents information telling if the cap 4 is protecting the medicine ejecting section 3 or not to the CPU 8.

As the sensor 5 recognizes that the cap 4 covers the medicine ejecting section 3, the air flow duct forming member 1 is released from a locked state of being prohibited from being fitted to and taken off from the inhaler body 2 so that the air flow duct forming member 1 can be removably fitted to the inhaler body 2.

When the cap 4 is opened and hence the cap 4 does not protect the medicine ejecting section 3 any longer, the sensor 5 cannot recognize that the cap 4 covers the medicine ejecting section 3. Then, the air flow duct forming member 1 is prohibited from being fitted to or taken off from the inhaler body 2. In other words, the medicine ejecting section 3 would not be damaged because the air flow duct forming member 1 can neither be fitted to nor taken off from the inhaler body 2. Additionally, the warning mechanism 7 displays a warning of prohibiting the air flow duct forming member 1 from being fitted to and taken off from the inhaler body 2 to notify the user of the prohibition.

Figure 1B:
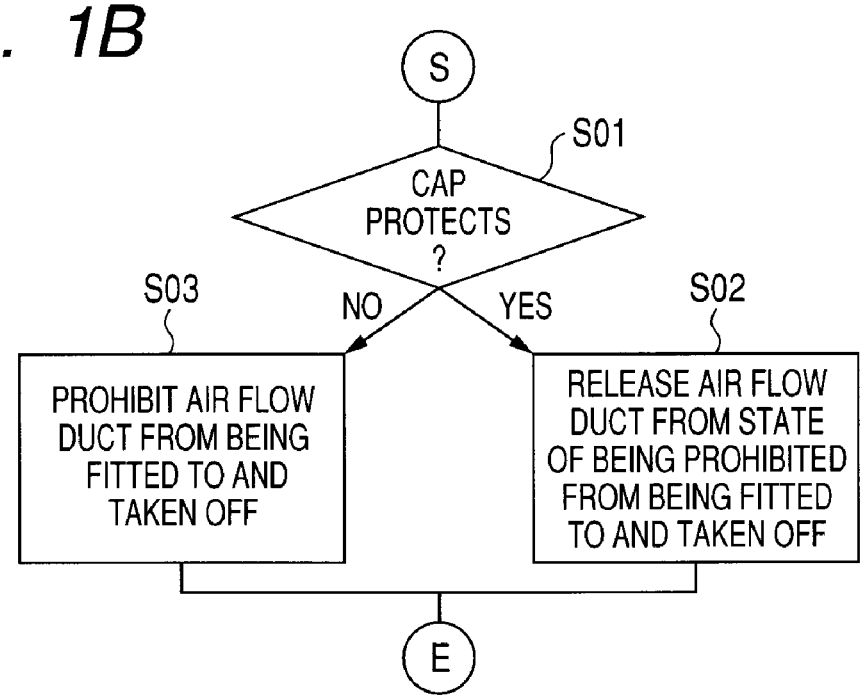

FIG. 1B is a flowchart illustrating the operation of the locking mechanism for prohibiting the air flow duct forming member from being fitted to and taken off from the inhaler body of the inhaler of FIG. 1A. Referring to FIG. 1B, the sensor 5 recognizes if the cap 4 for protecting the medicine ejecting section 3 is open or closed in Step S01.

If the sensor 5 recognizes that the cap 4 is closed to protect the medicine ejecting section 3, the air flow duct forming member 1 is released from a locked state of being prohibited from being fitted to and taken off from the inhaler body 2 in Step S02.

If the cap 4 is open and the medicine ejecting section 3 is not protected, the locking mechanism 6 prohibits the air flow duct forming member 1 from being fitted to and removed from the inhaler body 2 in Step S03.

Additionally, it may be so arranged that the warning mechanism 7 notifies the user that the air flow duct forming member 1 is prohibited from being fitted to and taken off from the inhaler body 2.

For the purpose of the present invention, "medicine" refers to not only medicinal compounds that provide pharmacological and physiological effects but also tasty and fragrant ingredients, aromatics, dyes and pigments. Additionally, for the purpose of the present invention, medicine may be liquid or powder.

For the purpose of the present invention, liquid medicine refers to liquid medicinal substance and liquid mediums that contain medicine. Liquid medicine may contain any additive (s). As for the state of medicine in liquid, the medicine may be dissolved, dispersed, emulsified, suspended or slurried. Preferably, the medicine may uniformly exist in liquid.

When liquid medicine is employed as medicine, the liquid major medium is preferably water or an organic compound. It is more preferably water from the viewpoint that the liquid medicine is administered to a living body.

EXAMPLE 2

Figure 2A:
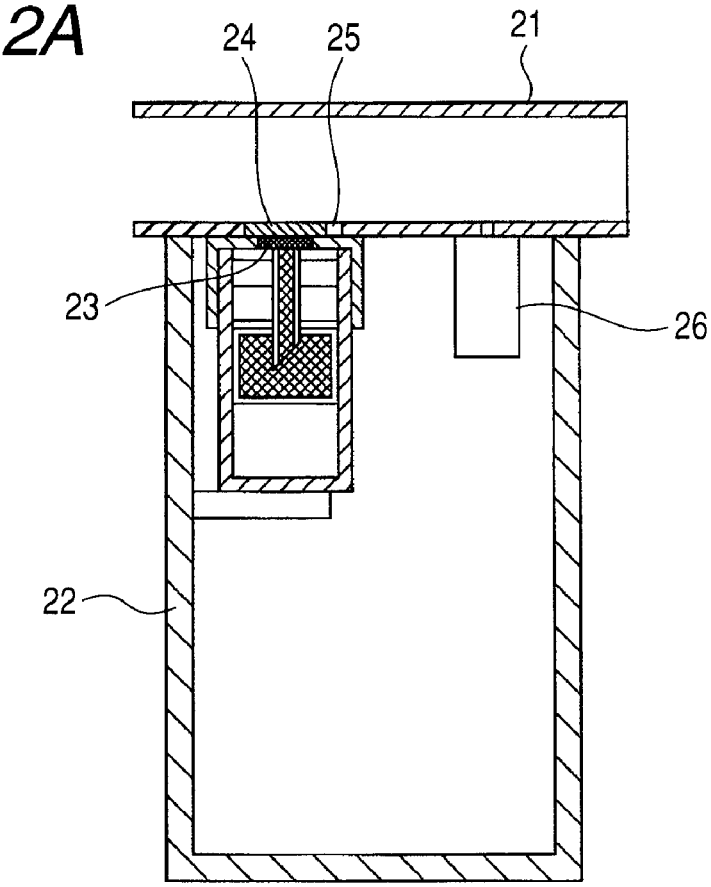

FIG. 2A is a schematic cross-sectional view of the inhaler of Example 2. The inhaler of this example includes an air flow duct forming member 21 and an inhaler body 22. The inhaler body 22 by turn includes a medicine ejecting section 23, a cap 24 for protecting the medicine ejecting section 23, an opening/closing mechanism 25 for opening and closing the cap 24 to protect the medicine ejecting section 23 and release the medicine ejecting section 23 from a protected state, and a sensor 26 for recognizing that the air flow duct forming member 21 is present or absent among others.

The air flow duct forming member 21 can be fitted to and taken off from (removably fitted to) the inhaler body 22.

The air flow duct forming member 21 is so arranged that the user can put it to and remove it from the inhaler body 22 by moving it horizontally or vertically or rotating it.

The sensor 26 that recognizes the presence or absence of the air flow duct forming member 21 recognizes that the air flow duct forming member 21 is present when the air flow duct forming member 21 is fitted to the inhaler body.

The sensor 26 that recognizes that the air flow duct forming member 21 is present or absent is typically formed by using a touch sensor or a photo-sensor that is adapted to transmit an electric signal that represents information telling if the air flow duct forming member 21 is fitted to the inhaler body 22 or not, to the CPU.

The cap 24 for protecting the medicine ejecting section 23 actually protects the medicine ejecting section 23 by entirely covering the medicine ejecting section 23 when the cap 24 is closed by the opening/closing mechanism 25.

The opening/closing mechanism 25 can drive the cap 24 to move by means of a motor. The opening/closing mechanism 25 can drive the cap 24 to move from a position where the cap 24 protects the medicine ejecting section 23 to a position where the cap 24 does not protect the medicine ejecting section 23 and vice versa.

When the air flow duct forming member 21 is fitted to the inhaler body 22, the medicine ejecting section 23 can be released from a state where it is protected by the cap 24. When, on the other hand, the air flow duct forming member 21 is not fitted to the inhaler body 22, the medicine ejecting section 23 is prevented from being damaged by the user because the cap 24 is protecting the medicine ejecting section 23. The timing of opening the cap 24 and hence releasing the medicine ejecting section 23 is not limited to immediately after the time when the sensor 26 recognizes that the air flow duct forming member 21 is fitted to the inhaler body 22. The inhaler of Example 2 has a feature that the sensor 26 recognizes that the air flow duct forming member 21 is fitted to the inhaler body 22 to allow the cap to be opened, and the cap may be opened actually immediately before the user inhales medicine from the inhaler.

Figure 2B:
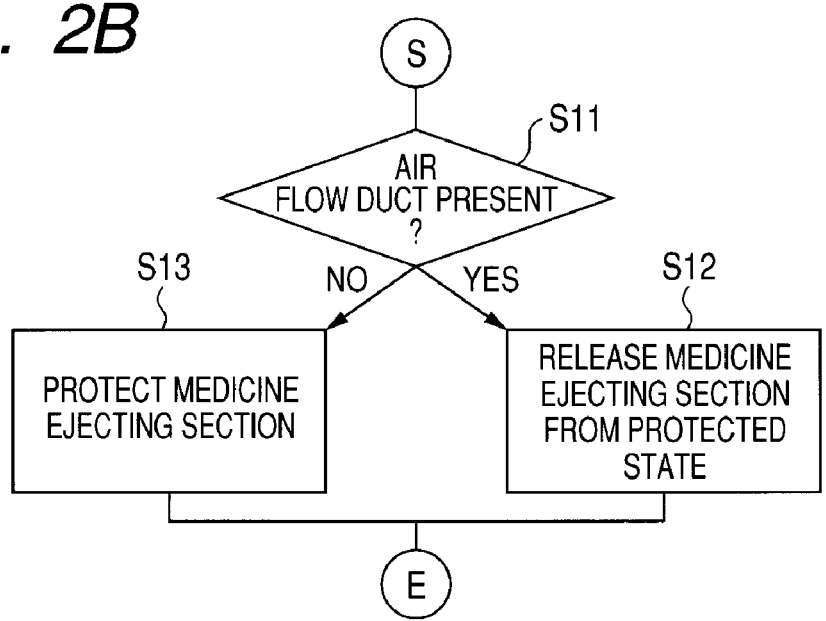

FIG. 2B is a flowchart illustrating a typical operation of the inhaler of FIG. 2A.

The sensor 26 recognizes the presence or absence of the air flow duct forming member 21 in Step S11. When the air flow duct forming member 21 is fitted to the inhaler body 22, the cap 24 is opened to release the medicine ejecting section 23 from the state of being protected in Step S12.

When the air flow duct forming member 21 is taken off from the inhaler body 22, the cap 24 is closed to protect the medicine ejecting section 23 in Step S13.

EXAMPLE 3

FIGS. 3 through 6B illustrate the inhaler of Example 3. The inhaler of this example includes a removable air flow duct forming member 31 and an inhaler body 32 as illustrated in FIG. 3.

Figure 4:
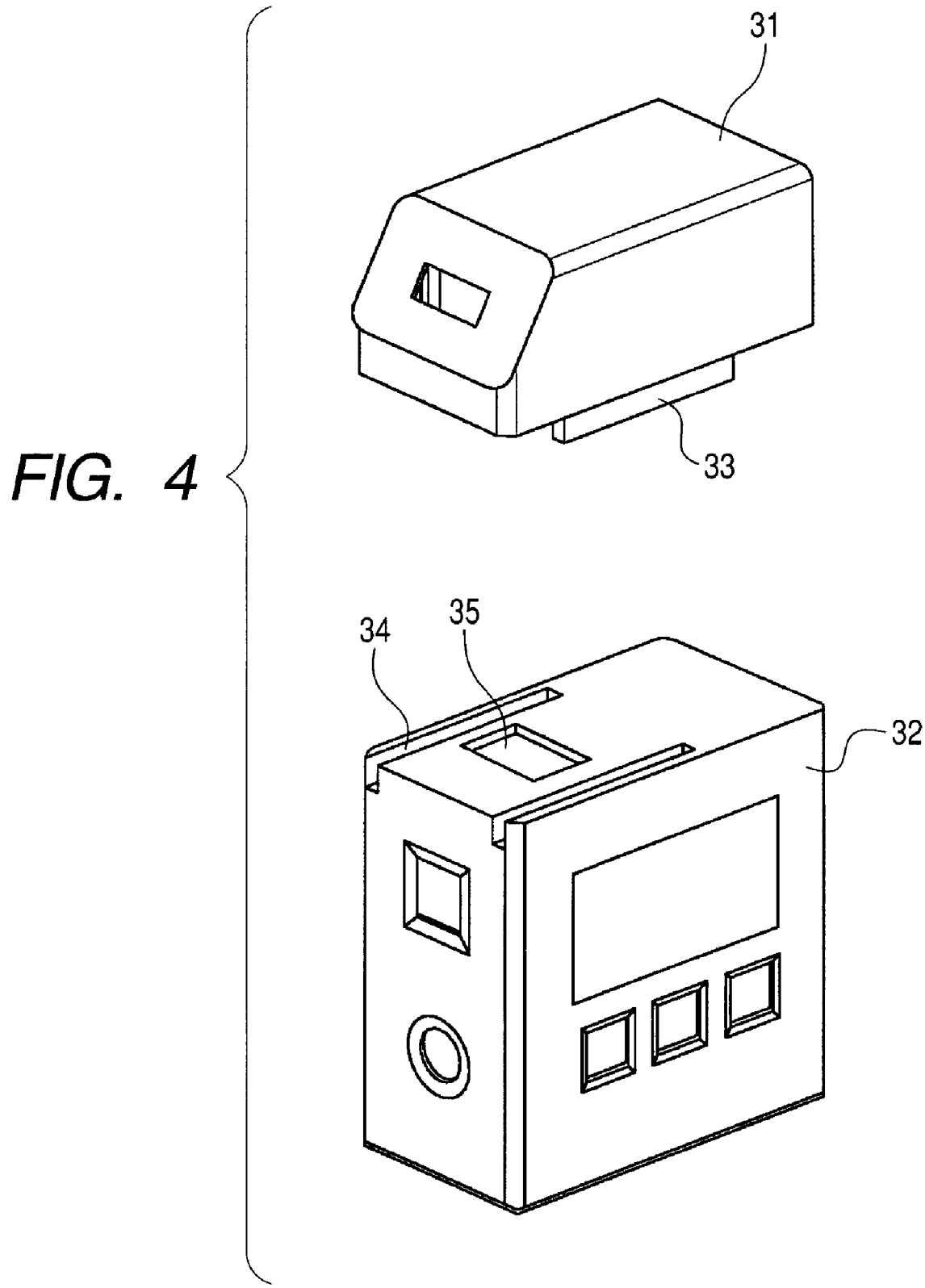
FIG. 4 is a schematic partial perspective view of the inhaler of FIG. 3 in a state where the air flow duct forming member is taken off from the inhaler.

FIG. 4 is a schematic partial perspective view of the inhaler of FIG. 3 in a state where the air flow duct forming member 31 is taken off from the inhaler body 32. The air flow duct forming member 31 is provided with a claw 33 so that the air flow duct forming member 31 can be fitted to and taken off from (removably fitted to) the inhaler body 32 by driving the claw 33 to move in the groove 34 formed in the inhaler body 32.

Ejected medicine passes through aperture 35 formed in the inhaler body 32.

FIGS. 5A and 5B schematically illustrate the inhaler body 32 from which the air flow duct forming member 31 is taken off. The inhaler body 32 by turn includes a medicine ejecting section 36, a cap 37 for protecting the medicine ejecting section 36 and an interlocking mechanism that includes a spring 38 linking the cap 37 and the inhaler body 32 among others.

When the air flow duct forming member 31 is taken off from the inhaler body 32, the cap 37 is driven to move by the urging force of the spring 38 and cover both the medicine ejecting section 36 and the aperture 35.

Thus, the movement of the cap 37 to cover the medicine ejecting section 36 is interlocked with the action of taking the air flow duct forming member 31 off from the inhaler body 32 so that the medicine ejecting section 36 is protected by the cap 37.

As the claw 33 is driven to move along the groove 34 in order to fit the air flow duct forming member 31 to the inhaler body 32, one of the lateral surfaces 39 of the claw 33 comes to abut the corresponding lateral surface 40 of the cap 37. As the air flow duct forming section 31 is driven to move against the spring 38 with force stronger than the urging force of the spring 38, the cap 37 is driven to move in a horizontal direction that is the same as the direction along which the air flow duct forming section 31 moves. FIGS. 6A and 6B illustrate a state where the air flow duct forming member 31 is completely mounted to the inhaler body 32.

As the air flow duct forming member 31 is completely mounted to the inhaler body 32, the medicine ejecting section 36, the cap 37 and the aperture 35 show a positional relationship as illustrated in FIGS. 6A and 6B and the medicine ejecting section 36 and the aperture 35 communicate with each other by way of the hole 41 of the cap 37.

As the claw 33 is driven to move along the groove 34 in the opposite direction in order to take the air flow duct forming member 31 off the inhaler body 32, the cap 37 is driven by the urging force of the spring 38 to move in the moving direction of the air flow duct forming member 31. As illustrated in FIG. 5A, the distance a from the claw 33 of the air flow duct forming member 31 to the rear end of the air flow duct is not less than the distance b from the front end to the medicine ejecting section 36 of the inhaler body 32. Therefore, the medicine ejecting section 36, the cap 37 and the aperture 35 come to show a positional relationship as illustrated in FIG. 5B before the air flow duct forming member 31 is completely taken off from the inhaler body 32 so that the cap 37 can safely protect the medicine ejecting section 36.

In this way, the medicine ejecting section 36 is protected and released from a protected state by the operation of removably fitting the air flow duct forming member 31 to the inhaler body 32.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2008-175333, filed Jul. 4, 2008, which is hereby incorporated by reference herein in its entirety.

What is claimed is:

1. An inhaler to be used by a user to inhale medicine, the inhaler comprising:
    an inhaler body having a medicine ejecting section for ejecting medicine;
    an air flow duct forming member having an inhalation port and adapted to be removably fitted to the inhaler body so as to form an air flow duct on the inhaler body in order to lead the medicine ejected from the medicine ejecting section to the inhalation port;
    a cap adapted to be freely opened and closed so as to protect the medicine ejecting section at rest;
    an opening/closing mechanism for opening and closing the cap; and
    a locking mechanism for prohibiting the air flow duct forming member from being fitted to and removed from the inhaler body when the cap is open and not protecting the medicine ejecting section.

2. The inhaler according to claim 1, further comprising:
    a warning mechanism for notifying the user that the user is prohibited from fitting the air flow duct forming member to and removing the air flow duct forming member from the inhaler body when the cap is open.

3. The inhaler according to claim 1, further comprising:
    a sensor adapted to recognize if the cap is open or closed and transmit information on the open or closed state of the cap to the locking mechanism by means of an electric signal,
    the locking mechanism being adapted to lock the air flow duct forming member to the inhaler body when the cap is open based on an output of the sensor.

* * * * *